US008545904B1

(12) United States Patent
Morse et al.

(10) Patent No.: US 8,545,904 B1
(45) Date of Patent: Oct. 1, 2013

(54) **TOPICAL COMPOSITION CONTAINING *CARAPA* (ANDIROBA) OIL FOR PSORIASIS AND OTHER RELATED DERMATOLOGICAL DISORDERS**

(75) Inventors: Tammy Jeanette Morse, Middletown, CT (US); Thomas Anthony Selmont, Hamden, CT (US)

(73) Assignee: Liquid Innovators, LLC, Wallingford, CT (US)

( * ) Notice: Subject to any disclaimer, the term of this patent is extended or adjusted under 35 U.S.C. 154(b) by 0 days.

(21) Appl. No.: 13/488,929

(22) Filed: Jun. 5, 2012

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS

| 5,958,421 | A | 9/1999 | Rouillard et al. |
| 7,147,854 | B2 | 12/2006 | Ye |
| 7,670,620 | B2 | 3/2010 | Meisner |
| 8,158,660 | B2 | 4/2012 | Cheng et al. |

FOREIGN PATENT DOCUMENTS

WO    WO 2006/007680 A1    1/2006

OTHER PUBLICATIONS

Habif TP, et al. Psoriasis and other papulosquarnotis diseases In Skin Disease: Diagnosis and Treatment, (2005) pp. 106-115. Philadelphia: Elsevier Mosby.
Gudjonsson JE, Elder JT. Psoriasis, in K Wolff et al., eds., Fitzpatrick's Dermatology in General Medicine, (2008), 7th ed., vol. 1, pp. 169-193: New York: McGraw-Hill Medical.
Nayak B, Kanhai J, Milne D, Pino Pereira L, Swanston W.H Experimental Evaluation of Ethanolic Extract of Carapa guianensis L.Leaf for Its Wound Healing Activity Using Three Wound Models, Evict. Based. Comple. Alt. Med. (2009), vol. 2011, Article ID 419612.
Sampogna F, Chren MM, Melchi CF, Pasquini P. Tabolli S, Abeni D Age, gender, quality of life and psychological distress in patients hospitalized with psoriasis, Br. J. Dermatot (Feb. 2006). 154 (2): 325-31. doi:10.1111/j.1365-2133.2005.06909.
Kemper M.D. M.P. H, Kathi 1., Clinical Information Summary of Calendula, The Long-wood HerbalTask Force, The Center for Holistic Pediatric Education and Research, 1999.
Krueger JG, Bowcock A. Psoriasis pathophysiology: current concepts of pathogenesis. Ann Rheum Dis. Mar. 2005;64 Suppl 2:ii30-6.
J.H. Costa-Silvaa, C.R. Limma, E.J.R. Silvaa, A.V. Araujob M.C.C. A. Fragrab A. Ribeiro e Ribeiroc, A. C. Arrudac, S.S.L. Lafayettea, B, A.G. Wanderleya Acute and subacute toxicity of the Carapa guianensis Aublet (Mellaceae) seed oil, Journal of Ethnopharmacology, vol. 116, Issue 3, Mar. 28, 2008, pp. 495-450.
Chainier F, Roussel D, Georges B, Meister R, Rouanetj L, Duchamp C, Barre H., PubMed, Lipids Oct. 2000; 35 (10):1 099-106.
Hay IC, Jamieson M, Ormerod AD., Arch Dermatol Nov. 1998;1 34(11):1349-52.
Graf J., Skin Therapy Lett 2000;5(4):3-5.
Akihisa T, Yasukawa K, Oinuma H, Kasahara Y, Yamanouchi S, Takido M, et al. Triterpene alcohols from the flowers of composite and their anti-inflammatory effects. Phytochemistry 1996; 43:1255-60.
Patrick K., Kumar S., Edwardson P, Hutchinson J. Induction of vascularization by an aqueous extract of the flowers of Calendula officinale L . The European marigold. Phytomedicirie 1996; 3.11-18.
Rao S., Udupa A., Ydupa S., Rao G., Kulkami D. Calendula and hypericum: two homeopathis drugs promoting wound healing in rats. Fitoterapia 1991; 62:508.
Kartikeyan S., Chaturvedi R. M., Narkar S. V. Effect of calendula on topic ulcers. Lepr Zrev 1990; 61:399.
Griffin WC: Classification of Surface-Active Agentsby 'HLB' Journal of the Society of Cosmetic Chemists 1 (1949): 311.

*Primary Examiner* — Michael Meller

(57) ABSTRACT

The subject of the invention is the use of a topical composition for the relief of dermatological disorders, with a primary intention or focus of treating symptoms associated with psoriasis and similar dermatological disorders and/or diseases.

1 Claim, 3 Drawing Sheets

| Figure 1 Typical Topical Cream or Lotion Formula |
| --- |
| Distilled Water 50-70% |
| Oils (Andiroba & Carrier) 5-17% |
| Emulsifier 2-10% |
| Preservative .5-1% |
| Other Ingredients (Inactive & Active) .5-1.9% |
| Fragrance .01-.1% |

| Figure 2 Clinical Study of Topical Composition ||||| 
|---|---|---|---|---|
| Subject / Age | #1 - 33yr old Male | #2 - 57yr old Female | #3 - 8yr old Male | #4 - 42yr old Female |
| Diagnosis | Plague Psoriasis | Plague Psoriasis | Localized Dermatitis | Eczema |
| Affected Area | Elbows, Face (neck, eyes, ears), Knees, | Knuckles on back of hands, Elbows, Knees, Shins | Face (around mouth) | Hands, Palms, Elbows |
| Duration of Disease | 15 years | 5-6 years | 2 months | 6 months |
| Severity/Symptoms | Heavy scaling & Inflammation on all affected areas, Extreme heat/water sensitivity to face, Deep red inflammation | Scaling, raised patches, severe red inflammation | Red, irritated skin, chapped skin, itchy | Inflamed, irritated raised rash, Itchy |
| Previous Therapy | Coal Tar, Topical & Oral Steroids, Unsupervised UV Therapy | Coal Tar, Topical Steroids | Moisturizing Lotion, Petroleum Jelly | Change in Diet, Allergy Medication (antihistamines) |
| Treatment Period | 3 Months | 6 Weeks | 3 Days | 1 Month |
| Results of Topical Composition | Reduced Scaling, Skin sensitivity eliminated, inflammation significantly reduced | Reduced Scaling, reduction in raised areas, inflammation significantly reduced | Skin return to normal state. Total relief of Redness, chapped itchy areas | Redness relieved, Itch relief, skin returned to near normal state |
| Post Treatment | Slow re-occurrence after 15 days | Some to little reoccurrence after several weeks | No recurring symptoms | Skin remained normal for several months |

Figure 3. Prior to composition being applied
Figure 4. After 3 days of treatment

TOPICAL COMPOSITION CONTAINING *CARAPA* (ANDIROBA) OIL FOR PSORIASIS AND OTHER RELATED DERMATOLOGICAL DISORDERS

FIELD OF INVENTION

The composition revolves around the treatment of the signs and symptoms of Psoriasis and other dermatological conditions in a topical application.

The focus of the invention is a formulation or composition utilizing *Carapa* refinements, and other natural botanical derivatives for the treatment of dermatological disorders.

BACKGROUND OF THE INVENTION

Psoriasis is an autoimmune disease that affects globally 1-3% of the population, 2-3% in the United States. Psoriasis is more common in adults than in children. It is equally common in women and men. Every year there is approximately 150,000 newly diagnosed cases of Psoriasis. Research shows that the signs and symptoms of psoriasis usually appear between 15 and 35 years of age with about 75% of cases developing into psoriasis before age 40. However, it is possible to develop psoriasis at any age. After age 40, a peak onset period occurs between 50 and 60 years of age.

Typically it has a physical manifestation of thick, red, patchy, scaly areas that occur on the epidermal layers of the skin due to skin cells that are mistaken by the immune system as dangerous free radical pathogens. The cause of the loss of control of keratinocyte turnover is unknown. However, environmental, genetic, and immunologic factors appear to play a significant role.

Psoriasis is not contagious; however, psoriasis has been linked to an increased risk of stroke and other health concerns. It has been well documented to effect health related quality of life to extent to other chronic diseases such as depression, hypertension, congestive heart failure, or type two diabetes. [Sampogna F, Chren M M, Melchi C F, Pasquini P, Tabolli 5, Abeni D (February 2006). "Age, gender, quality of life and psychological distress in patients hospitalized with psoriasis". Br. J. Dermatol. 154 (2): 325-31. doi:10.1111/j.1365-2133.2005.06909.x. PMID 16433804.]

Plaque, guttate, inverse, pustular and erythrodermic are generally the five different types or classes of Psoriasis. The most common form, plaque psoriasis (psoriasis vulgaris), is commonly seen as red and white hues of scaly patches appearing on the top first layer of the epidermis. Some patients, though, have no dermatological symptoms or have inconsistent growth and remission periods. Psoriasis most common form, plaque psoriasis also known as discoid psoriasis, accounts for 80-90% of all known instances in western society. It is typically found on the elbows, knees, scalp and lower back. Specifically, the epidermis is infiltrated by a large number of activated T cells, which appear to be capable of inducing keratinocyte proliferation. This is supported by histologic examination and immunohistochemical staining of psoriatic plaques revealing large populations of T cells within the psoriasis lesions. One report calculated that a patient with 20% body surface area affected with psoriasis lesions has around 8 billion blood circulating T cells compared with approximately 20 billion T cells located in the dermis and epidermis of psoriasis plaques. [Krueger J G, Bowcock A. Psoriasis pathophysiology: current concepts of pathogenesis. Ann Rheum Dis. March 2005; 64 Suppl 2:ii30-6.]

In normal skin growth, skin cells produced in the basal cell layer move up through the epidermis to the outermost layer, the stratum corneum. The process from cell birth to cell death takes about 28-30 days. When skin is damaged, the cycle runs much faster. In psoriasis patients, though there is no wound at the site of psoriatic lesions, skin cells called keratinocytes act in a regenerative manner. New skin cells are produced in 2-4 days, thus making it very difficult to shed old cells at an adequate rate. The elevated scaly lesions are a result of the buildup of cells. The white scale is the dead skin cells, and the redness a result of an increase in blood flow to areas of high cell division. Psoriasis is characterized by extreme epidermal hyper-proliferation, which is an excessive growth associated with incomplete and accelerated differentiation and noticeable inflammation of epidermis and dermis at local sites with development of neutrophil micro abscess and enhanced induction of cycling T lymphocytes.

The cause of psoriasis was initially thought to involve one of the mediators of hyper-proliferation. However, researchers began to focus on the immune system, after by chance it was discovered that cyclosporine with immunosuppressive effects significantly improved conditions in psoriasis patients. Thus, psoriasis is now viewed as an autoimmune disease.

There are many confirmed unique dermatological disorders or dermatitis that affects a significant percentage of the population and typically the average human will be affected by at least one type if not more of these disorders throughout their lifetime. Some of the more common epidermal conditions, skin cancer, eczema, various dermatitis, rosacea, etc. to list a few, are even more damaging to the mental well-being of the subject due to the high rate of depression and self-esteem issues. Most disorders do not have a specific cause or "trigger" nor do they have any cures to treat.

These other well documented disorders present themselves in numerous ways superficially, more commonly as red or discolored skin, inflamed and irritated localized areas, and dry flaky areas on the epidermis. Most dermatological disorders share many of the same signs and symptoms.

Subjects with skin conditions rely heavily on over the counter treatments (especially topical treatments) and home remedies to relieve the symptoms of skin disorders. This is partly caused by the high cost of medically overseen procedures and prescriptions that are accompanied by low success rates. Over the counter drugs, such as coal tar and Corticosteroids, also have adverse side effects as well as other troubling problems such as staining of clothes, noxious odors, and uncomfortable, disliked feel of the skin.

According to the US Food and Drug Administration, it has been well documented, and confirmed the side effects relating to the use of various OTC (Over the counter) and prescription treatments including skin atrophy and unwanted immunosuppressant consequences leading to fungal or bacterial infection, and general allergic reactions.

At the present time there are several prescription therapies for the treatment of Psoriasis:

Phototherapy or use of UV light is very common and usually the first line of prescription therapy. Most of these treatments have undesirable side effects such as burning, nausea, carcinogenesis, photo toxicity, and pruritus (itch). "Off Label" and other Prescription Drugs include Zidovudine (Retrovir), which is also the drug used to slow AIDS. Side effects involve a decrease in Red and White Blood Cell counts. Antithyroid Thioureylenes is used; the drug is used for hyperthyroidism. An example is propylthiouracil and methimazole (Tapazole). Side-effects include hypothyroidism. Capsaicin (Zostrix 0.025% cream) is approved for pain relief in rheumatoid arthritis, osteoarthritis, and neuralgia. The major side effect is a stinging sensation of the skin. Cyclosporine (Sandimmune) is approved for use in organ transplantation. Some side effects are potentially toxic which include headaches, gastrointestinal disturbances, hypertrichosis, paresthesias, and gingival hyperplasia. It is extremely important that nephrotoxicity be carefully monitored with this drug. Side-effects increase with length of time the drug is administered, so it is not an acceptable long-term therapy for patients. A new formulation called Neoral (approved for organ transplantation) may reduce toxicity, but further studies are needed. DAB3891L-2 is a cytotoxin that selectively attacks IL-2 receptors on cells and destroys them. Side effects include: flu like symptoms, pruritus, and transient transaminase elevation. Tacrolimus (Prolaf) is a macrolide antibiotic used to treat allograft rejection in liver transplant patients. Side effects are similar to Cyclosporine.

None of these Prescription drugs were designed with the intent to treat Psoriasis or other dermatological diseases.

The term topical composition refers to an amount of a compound herein that is sufficient to provide an effective treatment, as discussed below. It is understood that what comprises a topical composition in an effective amount that may be a lesser amount of the compound when it is administered in combination with another substance than when utilized alone.

As referenced in patent application Ser. No. 12/437,704 The term "treating" (and corresponding terms "treat" and "treatment") includes palliative, restorative, and preventative treating of a subject. The term "palliative treating" refers to treatment that eases or reduces the effect or intensity of a condition in a subject without curing the condition. The term "preventative treating" refers to treatment that prevents the occurrence of a condition in a subject. The term "restorative treating" ("curative") refers to treatment that halts the progression of, reduces the pathologic manifestations of, or entirely eliminates a condition in a subject.

Topical epicutaneous compositions are commonly used to treat and repair diseased and damaged skin. They come in many forms or classes such as ointments, creams, lotions, gels, etc. Compositions are comprised of various ingredients to act as a direct carrier of an active ingredient(s) or substance(s) to a directed or targeted area of the epidermis.

*Carapa guianensis*, also known as Andiroba, has been used by Amazon Rainforest indigenous communities, particularly the forest dwellers named Caboclos, for the treatment of coughs, convulsions, skin diseases, arthritis, rheumatism, ear infections, to heal wounds and bruises and most notably as an insect repellent.

*Carapa* is a genus in the mahogany family Meliaceae. The *Carapa* species become medium to large sized trees growing at 30 m tall; common names include Andiroba and Crabwood. A member of the Meliaceae family, *C. guianensis* is widely distributed throughout eastern Amazonia, the Guianas, Trinidad, Central America up to Nicaragua, and Africa. Typically grows in the marshlands or other hydromorphic soils. The bark is grey to brown with a smooth to flaky appearance. The seeds originate from the fruit which flower from August to October and the fruit matures January through April. The tree production of fruit vary from year to year, some years the tree may have an abundant yield and other years they may produce minimal harvest. This phenomenon is unknown. The oil is a direct result of either mechanical or chemical extraction of the cultivated seeds.

*Carapa* Seeds are composed of 74% fatty deposit reserve within the skin or shell, the remaining 26% is skin or outer shell. The oil is a direct refinement of the fatty deposits located internal to the seed. Oil becomes solid at temperature below 25° C. The following chemicals were isolated and confirmed in *Carapa* genus of plants:

Acids: arachidic acid, hexadecenoic acid, linoleic acid, oleic acid, palmitic acid, palmitoleic acid, stearic acid, myristic acid Tetranortriterpenoids (Limonoids): 6-alpha-acetoxy-epoxyazadiradione, 6-alpha-11-beta-diacetoxygedunin, 6-alpha-acetoxygedunin, 6-alpha-hydroxygedunin, 6-alpha-1'-beta-dihydroxy 7-deacetoxygedunin, 6-alpha-7-alpha-11-beta-trihydroxy 7-deacetoxygedunin, 7-alpha-hydroxy 7-deacetoxygedunin, 6-betaacetoxygedunin, 6-beta-11-beta-diacetoxygedunin, 11-beta acetoxygedunin, 7-deacetoxy-7-oxogedunin, 7-desacetoxy-7-ketogedunin, epoxyazadiradione, and andirobin Andirobin is a unique natural Tetranortriterpenoids found only in the extracts of the *Carapa* tree.

The group of phytochemicals called Tetranortriterpenoids, here in called TNTP, are proven to be the main source of healing or otherwise known as the documented active ingredient. They have been proven to be the biologically active ingredients based on several wound healing models as well as extensive study by isolating these chemicals and performing in vivo experiments on rats. [International Publication WO2006/007680 A1 26 Jan. 2006]

Although the international publication claims anti-allergenic and anti-histaminic activity from the TNTP they have completely failed to recognize the benefits of the compound for already established skin disorders such as psoriasis. They emphasize oral medication or topical cream for the sudden onset of inflammation due to histamine reaction, or simply an allergic reaction. Our personal in vivo studies on human subjects prove therapeutic qualities for illnesses derived from within the body, by applying a given amount of topical cream to an affected location on our subjects at a consistent rate.

The international publication also clearly recognizes the immune suppressant qualities of TNTP but does not consider their potential in treatment. The biggest discovery in Psoriasis treatment over the last decade is the fact of origin starts in the immune system.

In addition to the TNTP's, Andiroba oil is also a significant source of omega fatty acids. The acceleration in the healing of damaged skin is performed by the active compound myristic acid present in Andiroba oil, this acid forms one of the vital chemical building blocks for an organic enzyme which is the main structure linking together many of the proteins which form the tissues on the skin outer layer. This chemical also signals skin cells to stop growth and this factor is useful when the oil is used in the treatment of psoriasis, the signal results in the prevention of skin scaling which is quite common in many skin disorders. The restoration of a normal life cycle to skin cells is also another important function performed by one of the many fatty acids in Andiroba oil, the linolenic acid maintains normal life cycle in growth and death of skin cells. Psoriasis for example, can be cured as a result of the halting of the uncontrolled growth in the skin cells due to the presence of this chemical. The chemical also aids in putting a stop to the uncontrolled growth of all pigment producing cells which contribute to the cause of age spots in older people.

Andiroba Oil has multiple names and alias throughout different cultures, countries and regions. *Carapa* oil, Karaba oil, Crabwood oil, Crab oil to list a few.

*Carapa guianensis* seed oil was evaluated for its acute and sub-acute toxicity (30 days) by the oral route in wistar rats. In the acute toxicity test, SO (0.625-5.0 g/kg, n=5/sex) did not produce any hazardous symptoms or deaths . . . . In conclusion, acute and sub-acute administration of *Carapa guianen-*

*sis* seed oil did not produce toxic effects in male wistar rats. Overall Carapa seed oil is found to be nontoxic or of ultra-low toxicity.

Grape seed extract has been well documented with numerous existing patents pertaining to skin treatment and growth. Angiogenesis, the process in which the vascular system grows and expands, and hyper proliferative wound closure occur from grape seed Proanthocyanidins by effecting vascular endothelial growth factors thus essentially speeding up the overall recovery of wounds. This makes an excellent secondary active ingredient to the TNTP component from in Andiroba oil.

The carrier oils added to the composition reinforces the moisturizing and natural state of the skin, as well as providing a highly desired feel or touch to the skin. The cosmetic industry has a large variety of highly desired and prized carrier oils that will couple nicely with Andiroba oil and the other ingredients. We chose grape seed oil in our test compositions due to its high quality, domestic availability, and cost.

The grape seed oil was infused with several herbs. *Calendula* Calenduleae, Chamomile Asteraceae, and Lavender Lamiaceae, were obtained from a local retailer and allowed to sit or infuse in the grape seed oil for not less than 72 hours. All three herbs are known for their medicinal properties particularly their ability to soothe irritated skin.

According to the Department of Dermatology, Aberdeen Royal Infirmary, Foresthill, Scotland, the following randomized trail of aromatherapy is successful treatment for alopecia greata. [Hay I C, Jamieson M, Ormerod A D., Arch Dermatol 1998 November; I 34(11):1349-52.] A randomized double blind, controlled trial of 7 month duration, with follow up at 3 and 7 months. Tests were conducted at Dermatology outpatient department. Eighty six patients diagnosed as having alopecia greata, divided into two groups. The active group massaged essential oils (thyme, rosemary, lavender, and cedarwood) in a mixture of carrier oils Jojoba and grape seed) into their scalps daily. The control groups used only carrier oils for their massage, also-daily. The outcome measures: Treatment success was evaluated on sequential photographs by 2 dermatologists (I.C.H.) and (A.D.O.) independently. The degree of improvement was measured by 2 methods, a 6-point scale and computerized analysis of traced areas of alopecia. Nineteen (44%) of 43 patients in the active group showed improvement compared with 6 (15%) of 41 patients in the control group (P=0.008). An alopecia scaled was applied in blinded observers on sequential photographs and was shown to be reproducible with good interobserver agreement (kappa=0.84). The degree of improvement on photographic assessment was significant (P=0.05). Demographic analysis showed that the 2 groups were well matched for prognostics factors. The conclusion, the results show aromatherapy to be a safe and effective treatment for alopecia greata. Treatment with these essential oils was significantly more effective than treatment with the carrier oil alone.

The following demonstrates how the cold acclimation or grape seed oil feeding affects the phospholipid corn-position and mitochondria function in duckling skeletal muscle. [Chainier F, Roussel D, Georges B, Meister R, Rouanetj L, Duchamp C, Barre H., PubMed, Lipids 2000 October; 35 (10):1 099-106]. The phospholipid fatty acid (FA) composition and functional properties of skeletal muscle and liver mitochondria were examined in cold-acclimated (CA, 4 degrees C.) ducklings. Phospholipid FA of isolated muscle mitochondria from CA birds were longer and more unsaturated than those from thermo neutral (TN, 25 degrees C.) reared ducklings. The rise in long-chained and polyunsaturated FA (PUFA, mainly 20:4n-6) was associated with a higher State 4 respiration rate and a lower respiratory control ratio (RCR). Haptic mitochondria, by contract, were much less affected by cold acclimation. The cold-induced changes in phospholipid FA profile and functional properties of muscle mitochondria were reproduced by giving TN ducklings a diet enriched in grape seed oil (GO, rich in n-6 FA), suggesting a causal relationship between the membrane structure and mitochondrial functional parameters. However, hepatic mitochondria from ducklings fed the Go diet also showed enrichment in long-chain PUFA but 3 Jul. 8, 2004 opposite changes in their biochemical characteristics (lower State 4, higher RCR). It is properties by membrane lipid compositions between skeletal muscle and liver may depend on muscle-specific factors possibly interacting with long-chain PUFA and affecting the proton leakiness of mitochondrial membranes.

Chamomile is used on the skin for many different problems including poison ivy, chicken pox, diaper rash, and other kinds of rashes. In addition, it is used for eczema, hemorrhoids and cuts or scrapes. Studies have proven that chamomile may decrease irritation and swelling from rashes. Important flavonoids have been identified in Chamomile including apigenin, luteotin, and quercetin. Recent research indicates that they display more or less inhibiting effects on certain malignant cell proliferation in vitro. [Agullo G, Gamet-Payrastre L, et al. Relationship between flavonoid structure and inhibition of phosphatidylinositol 3-kinase: a comparison with tyrosine kinase and protein kinase C inhabitation. Biochem Pharmacal].

The flowers of *calendula* og. *calendula offinicalis* contains sesquiterpene and flavonoid glycosides, triterpenoid saponins, sterols, fatty acids, carotenoids and other compounds. In vitro, calendula extracts displays uterotonic activity in isolated animal uteri. Data on antimicrobial effects are conflicting, but tend not to support use of *calendula* as an antimicrobial agent. In animals, calendula exerts sedative effects and synergistic effects with barbiturates in animal models. In two Polish studies from the 1960's, *calendula* exerted some estrogenic effects in ovariectomized mice. *Calendula* demonstrated moderate anti-inflammatory activity in several animal studies. *Calendula* extracts had anti-tumor effects in two studies in mice. In humans, Anecdotal reports and case series claim herbal mixtures including *calendula* can help heal gastric and duodenal ulcers and exert anti-inflammatory and wound healing effects. There are no controlled trials evaluating *calendula* use as a sedative, antimicrobial, estrogenic agent, uterine tonic, anti-tumor agent or vulnerary. [Kemper M. D. M. P. H, Kathi 1., Clinical Information Summary of *Calendula*, The Long-wood Herbal Task Force, The Center for Holistic Pediatric Education and Research, 1999].

Herbs have been used in clinical medicine for thousands of years. However, it is only in recent times that we have been able to employ scientific methods to prove the efficacy of many of these herbs and to give us a better understanding of their mechanisms of action. This article will focus on the use of herbs in various dermatological conditions characterized by inflammation and pruritus. Topical preparations of many of these herbs are more common-place in Europe. However, their availability is increasing in the US. As this is occurring we are witnessing a growing marriage between alternative and traditional medicines. [Graf J., Skin Therapy Lett 2000; 5(4):3-5].

The triterpene alcohols from *calendula* and other members of the daisy family have shown anti-inflammatory activity in the experimental mouse model. [Akihisa T, Yasukawa K, Oinuma H, Kasahara Y, Yamanouchi S, Takido M, et al.

Triterpene alcohols from the flowers of composite and their anti-inflammatory effects. Phytochemistry 1996; 43:1255-60].

One study reported enhanced vascularization in tissue cultures treated with a freeze-dried aqueous extract of *calendula*. [Patrick K., Kumar S., Edwardson P, Hutchinson J. Induction of vascularization by an aqueous extract of the flowers of *Calendula officinale* L. The European marigold. Phytomedicine 1996; 3:11-18]. Among rats with surgical wounds, an ointment containing 5% of the flower extract of *calendula* plus allantoin significantly speeded healing. [Kloucheck-Popova E., Popov A, Pavlova N., Krusteva S., Influence of the physiological regeneration and epithelialization using fractions isolated from *Calendula officinalis*. Acta Physiol Pharmacal Buig 1982; 8:63-7]. Other studies have shown that rats improved wound healing with 60% alcohol solution of *calendula* flowers. [Rao S., Udupa A., Ydupa S., Rao P., Rao G., Kulkarni D. *Calendula* and *hypericum*: two homeopathic drugs promoting wound healing in rats. Fitoterapia 1991; 62:508]. There is a long tradition and numerous case reports if using *calendula* based ointments for wound healing and hemorrhoids. Among adults suffering from leprosy, an ointment containing 10% *calendula* extract appeared to help heal chronic skin sores and prevent-additional infections. [Kartikeyan S., Chaturvedi R. M., Narkar S. V. Effect of *calendula* on topic ulcers. Lepr Zrev 1990; 61:399]

The therapeutic properties of Lavender include: Antiseptic, analgesic, anti-convulsant, anti-depressant, anti-rheumatic, anti-toxic, anti-spasmodic, anti-inflammatory, emmenagogue, anti-toxic, carminative, deodorant, diuretic, nervine, restorative, sedative, insecticide and tonic. Lavender oil has in vitro antimicrobial activity against bacteria, fungi, and some insects. The essential oil exerts spasmolytic activity in smooth muscle in vivo, supporting its historical use as a digestive aid. Over 150 compounds have been isolated from the oil. Although the chemical compositions of these oils are complex, the biological activities of the major chemical species present have been evaluated.

The discovery of a true cure for psoriasis is on the horizon however there is no accurate estimate of when this discovery will be made. The composition explained herein will provide a method of treatment and relief.

SUMMARY OF THE INVENTION

The present invention here is a completed topical agent that delivers phytochemical compounds with proven track records to targeted epidermal layers to relieve the complex symptoms of Psoriasis and many skin disorders. The topical composition utilizes a mixture of two oils, one being Andiroba Oil, the other being simply a carrier oil, Grape seed extract, *Calendula*, Chamomile, Lavender, Distilled Water, an emulsifying agent, a preservative, and a fragrance.

DETAILS OF THE INVENTION

After initial discovery of TNTP and the fatty acids contained in Andiroba oil, a strategy was devised to convert oil into a topically applied composition. A typical topical composition contains three main ingredients, an emulsifier, water and oil otherwise known as water in oil emulsion or oil in water emulsion. See FIG. 1. The herbs *Calendula*, Lavender and Chamomile were placed in the grape seed oil to allow for infusion to take place over a period of not less than 72 hours. The emulsifier acts as a chemical bond using the HLB system to lock oil and water molecules together. This system is described in Medical Journal titled "Development and Evaluation of Emulsions from *Carapa guianensis*. An HLB (Hydrophilic-Lipophilic Balance) surfactant is the measure of the degree to which it is hydrophilic or lipophilic, thus described by Griffin, see [Griffin W C: "Classification of Surface-Active Agents by 'HLB,'" Journal of the Society of Cosmetic Chemists 1 (1949): 311]. It was discovered that the HLB factor for Andiroba Oil and Grape seed Oil as a carrier is 16.7. Utilizing this knowledge we emulsified distilled water and the above referenced oils to generate a rich stable cream or lotion. We then added to the emulsion while in the cooling stage, grape seed extract, a preservative along with fragrance oil. The ingredients used were obtained by reputable and certified suppliers. The final formula utilized ECOMulse as the emulsifier, a well-known product in lotion development. ECOMulse is combination of Glyceryl Stearate, Cetearyl Alcohol, and Sodium Stearoyl Lactylate. In addition, the ingredients Citric Acid and Silver Citrate were included as the preservative to maintain an acceptable level of microbial, viral, fungal activity. A light fragrance was added to the final product for scent.

After several formulations the final product was used in a closed study to develop results of the therapeutic qualities of our composition. The studies were conducted on human subjects suffering from varying degrees and types of psoriasis, also some subjects were affected by other more common dermatological disorders such as eczema, epidermal hyperplasia, skin inflammatory elements and other dermatitis. The results varied from subject to subject; although, every subject produced positive results in treating the dermatological symptoms or elements. FIG. 2 summarizes the results of the study During the study, the subjects were given a sample of four ounces to be applied at minimum of twice daily, and not to exceed five times daily to the affected area. The composition was applied to the skin; each dispensed dosage contained approximately 6 cc of product. The product was massaged directly into the problem area and allowed to absorb naturally. The study varied from three days to three months with positive results being documented in as little as three days. It was also documented that subjects with severe cases of plaque psoriasis saw significant improvements after three weeks of use.

The test subjects discontinued use and the chart, FIG. 2, also details that outcome, which varied from subject to subject. The individuals with non-psoriatic issues witnessed no immediate recurrence and the Psoriasis patients witness a slow recurrence after weeks of discontinuing the composition. The results were very promising given only four individuals were studied. It has been proven to treat the symptoms of most dermatological disorders and in certain situations even cure acute dermatitis'.

BRIEF DESCRIPTION OF DRAWINGS

FIG. 1 Typical Topical Cream or Lotion Formula. This general formula is what was used in the treatment trials depicted in FIG. 2 and as discussed above.

FIG. 2 Clinical Study of Topical Composition. A table that helps to better understand the subjects being tested and the results of the in house clinical study that was completed.

FIG. 3 Photograph taken prior to composition being applied to subject #3, an 8 year old male as referenced from FIG. 2

FIG. 4 Photograph results post 3 days of treatment to subject #3

What is claimed:

1. A topical composition for treating psoriasis, eczema or cellulitis consisting essentially of therapeutically effective amounts of andiroba seed oil, grape seed oil, *calendula*, chamomile and lavender.

\* \* \* \* \*